Aug. 5, 1952 R. L. BYRUM Plant Pat. 1,118
ROSE PLANT
Filed Aug. 20, 1951
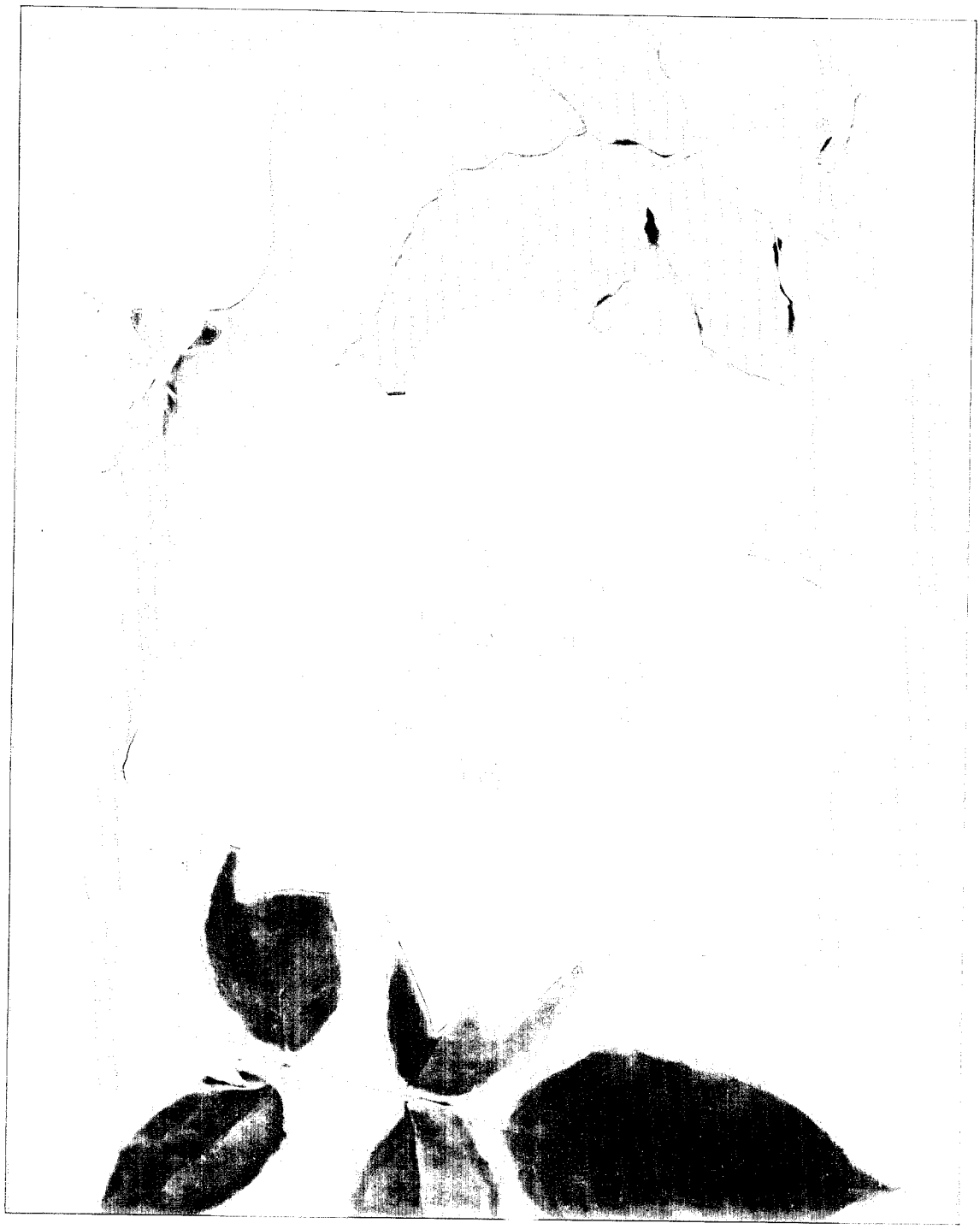
Inventor.
R. L. Byrum
By: Robbins Robb
Attorneys.

Patented Aug. 5, 1952

Plant Pat. 1,118

UNITED STATES PATENT OFFICE 1,118

ROSE PLANT

Roy L. Byrum, Richmond, Ind., assignor to Joseph H. Hill Company, Richmond, Ind., a corporation of Indiana Application August 20, 1951, Serial No. 242,749

1 Claim. (Cl. 47—61)

The present invention relates to a new and distinct variety of rose plant of the hybrid tea class, originated by me by crossing an unnamed and unpatented white sport of "Better Times" (Plant Patent No. 23), with the well-known variety "Snow White" (Plant Patent No. 348), the unnamed white sport being used as the seed parent and being identified in my research records and test plots as #44E.

The primary objective of this cross was to obtain a new variety having features which constitute an improvement over the usual caracteristics of "Snow White" and of "Peter's Briarcliff" (unpatented), which my new variety most nearly resembles. This objective was fully achieved, as evidenced by the fact that although the foliage of my new variety is similar to that of "Snow White," the blooms are larger and much more fragrant, and in addition, the new variety is a stronger grower and tends to produce stems longer than those of "Snow White."

As compared with "Peter's Briarcliff," my new variety produces blooms of larger size and which are longer-lasting than those of "Peter's Briarcliff," and the blooms of my new variety are also much more uniform in color from bloom-to-bloom on the same plant, as well as from one plant to another. In other words, each bloom of my new variety looks practically like every other bloom, whereas the blooms of "Peter's Briarcliff" usually vary considerably in color, and in group or greenhouse plantings, often appear to be like a lot of mixed plants of different varieties or of substantially different shades of color.

The principal distinguishing characteristics which are present in my new variety and which constitute an unusual and improved combination heretofore unknown in the class of Hybrid Tea roses, are as follows:

(1) Vigorous growth, tending to produce long stems;

(2) Materially improved resistance to mildew and blackspot;

(3) Relatively large blooms of Phlox Pink color in general tonality, and of relatively long-lasting quality, with marked resistance to heat which does not affect the size of the blooms, thereby making this variety a very good "hot weather" rose;

(4) Exceptionally pronounced fragrance of the blooms; and (5) Uniformity of color of the blooms on the same plant, as well as on different plants.

Asexual reproduction of my new variety by cuttings, grafting and budding, as performed at Richmond, Indiana, shows that the foregoing characteristics come true to form, and are established and transmitted through succeeding propagations.

The accompanying drawing shows specimen flowers of the new variety in the tight bud, partly open and fully open stages of development, as well as front and reverse sides of typical specimen leaves, and also a short section of a specimen stem showing a typical thorn arrangement.

The following is a detailed description of the new variety, with color terminology in accordance with Wilson's Horticultural Colour Chart, except where specifically noted as being in accordance with Koster's Color Guide or Ridgway's Color Standards and Nomenclature:

Type: Greenhouse; for cut flowers.
Class: Hybrid tea.
Parentage: Seedling.
*Seed parent.*—An unnamed white sport of "Better Times."
*Pollen parent.*—"Snow White."
Propagation: Holds its distinguishing characteristics through succeeding propagations by cuttings, grafting and by budding.

*Flower*

Locality where grown and observed: Richmond, Indiana.
Flowers borne: Singly to stem; on strong, long stems.
Quantity of bloom: Abundant in greenhouse.
Continuity: Continuous.
Fragrance: Strong; tea.
Bud:
*Peduncle.*—Long; heavy; erect; Fern Green, Plate 0862; smooth; numerous Chartreuse Green, Plate 663/3, prickles.
*Before calyx breaks.*—Size—medium to large. Form—long; pointed; with a conspicuous neck; with foliaceous appendages on the surface of the bud; with slender, much-cut, bristle-like foliaceous parts extending beyond the tip of the bud equal to ¾ or more of its length.
*As calyx breaks.*—Color—Spinel Red, Plates 0023/3 to 0023/2.
*As first petal opens.*—Size—large. Form—long; pointed. Color—outside: Neyron Rose, Plate 623/2 overlaid with 623/1; inside: Rose Madder, Plate 23/2 penciled with 23/1.
*Opening.*—Opens up well.

Bloom:

*Size, when fully open.*—Very large; 4 inches to six inches.

*Petalage.*—Double; from 40 to 45 petals arranged irregularly.

*Form.*—Full at first; becoming open; petals being at first tightly rolled outward; becoming later, at maturity, loosely rolled outward.

Petals: Thick; leathery; with inside satiny and outside shiny.

*Shape.*—Outside—obovate with apex flat. Intermediate—obovate with apex flat. Inside—obovate; irregular with one or two notches.

This description of a newly opened flower was made from a rose grown in a greenhouse at Richmond, Indiana:

*Color.* — Outside petal — outside surface: Phlox Pink, Plate 625/3, penciled with 625/2; inside surface: Phlox Pink, Plate 625/3, penciled with 625/1. Intermediate petal—outside surface: Phlox Pink, Plate 625/3 through 625/2; Inside surface: Phlox Pink, Plate 625/2. Inner petal—outside surface: Phlox Pink, Plate 625/2; some petals having a white stripe in center; inside surface: Phlox Pink, Plate 625/2; some petals having a white stripe in center.

This description was made from a rose that was open for three days in a greenhouse at Richmond, Indiana:

*Color.*—Outside petal—outside surface: almost white with Rose Pink shading, Plate 427/3; inside surface: Rose Pink, Plate 427/3. Inside petal—outside surface: Phlox Pink, Plate 625/2; some petals having a white stripe in center; inside surface: Phlox Pink, Plate 625/2; some petals having a white stripe in center.

*General color effect.*—Newly opened flower—Phlox Pink, Plate 625/2. Three days open—Phlox Pink, Plate 625/2.

*Behavior.*—Persist.

*Flower longevity.*—Cut roses grown in greenhouse—4 to 5 days.

*Reproductive organs*

Stamens: Many; arranged irregularly about pistils.

Filaments: Long; white, most with anthers.

Anthers: Medium size; all open at once; Yellow Ochre, Plate 07/2.

Pollen: Abundant; Spanish Orange, Plate 010.

Pistils: Medium in number.

Styles: Very uneven; medium length; thin; bunched.

Stigma: White.

Ovaries: All enclosed in calyx.

Hips: Ovoid; with inconspicuous neck; smooth.

Sepals: Permanent; long; spear-shaped. Color—inside: Lettuce Green, Plate 861/3, overlaid with white fuzz, outside: Lettuce Green, Plate 861/3, overlaid with 861/1.

*Plant*

Foliage:

*Leaves.*—Compound of 5 to 7 leaflets; very abundant; large; leathery.

*Leaflets.*—Shape—ovoid with apex mucronate. Base—round. Margin—simply serrate.

*Color.*—Mature—upper surface: near Taxus Green, Plate No. 81 (Koster); under surface: Apple Green, Plate No. 77, (Koster). Young—upper surface: near Claret Brown, Plate I (Ridgway); under surface: near Claret Brown, Plate I (Ridgway).

*Rachis.*—Medium heavy. Upper side—grooved; hairy. Under side—extremely smooth.

*Stipules.*—Medium length; medium width; with short points turning out at an angle of less than 45°.

*Disease.*—Resistant to mildew and blackspot.

Growth:

*Habit.*—Bush; upright; branched.

*Growth.*—Vigorous.

*Canes.*—Heavy.

*Main stems.*—Color—Spinach Green, Plate 0960; some canes overlaid with Tobacco Brown, Plate No. 88, and Fawn, Plate No. 89 (Koster). Thorns — several; medium length; hooked downward; round base. Prickles—none.

*Branches.*—Color—Lettuce Green, Plate 861. Thorns — several; medium length; hooked downward; round base. Color—Snuff Brown, Plate XXIX (Ridgway). Prickles—none. Hairs—none.

*New shoots.*—Color—Scheeles Green, Plate 860/1. Thorns—several; medium length; hooked downward; narrow base. Prickles—none. Hairs—none.

I claim:

A new and distinct variety of rose plant of the hybrid tea class, as herein shown and described, characterized as to novelty by its vigorous growth and long stems, by its resistance to mildew and blackspot, by its relatively large, long-lasting and heat resistant blooms of Phlox Pink color, by their strong tea fragrance, and by the uniformity of color of the blooms on the same plant and on different plants.

ROY L. BYRUM.

No references cited.